United States Patent [19]

Nishimura et al.

[11] Patent Number: 5,379,774
[45] Date of Patent: Jan. 10, 1995

[54] MEASUREMENT OF ARTERIAL ELASTICITY AND THE FREQUENCY CHARACTERISTIC OF THE COMPLIANCE OF AN ARTERY

[75] Inventors: Masatoshi Nishimura; Masaaki Takahashi; Yasushi Orihashi, all of Tokyo, Japan

[73] Assignee: Sankyo Company Limited, Tokyo, Japan

[21] Appl. No.: 218,022

[22] Filed: Mar. 25, 1994

Related U.S. Application Data

[63] Continuation-in-part of Ser. No. 695,008, May 3, 1991, abandoned.

[30] Foreign Application Priority Data

Oct. 23, 1990 [JP] Japan ................... 2-284572

[51] Int. Cl.$^6$ ................................ A61B 5/02
[52] U.S. Cl. ................... 128/666; 128/667; 128/694
[58] Field of Search ................... 128/633–634, 128/664–667, 672, 677–683, 687–690, 691, 694, 713

[56] References Cited

U.S. PATENT DOCUMENTS

| | | |
|---|---|---|
| 3,638,640 | 2/1972 | Shaw . |
| 3,647,299 | 3/1972 | Lavallee . |
| 3,799,672 | 2/1974 | Vurek . |
| 4,030,485 | 6/1977 | Warner ................... 128/667 |
| 4,407,290 | 10/1983 | Wilber . |
| 4,714,341 | 12/1987 | Hamaguri et al. ................... 356/41 |
| 4,819,752 | 4/1989 | Zelin . |
| 4,883,353 | 11/1989 | Hausman et al. . |

FOREIGN PATENT DOCUMENTS

| | | |
|---|---|---|
| 0380664 | 8/1990 | European Pat. Off. . |
| 0426358 | 5/1991 | European Pat. Off. . |
| 0475631 | 3/1992 | Japan ................... 128/666 |
| 4288130 | 10/1992 | Japan ................... 128/667 |
| 8201948 | 6/1982 | WIPO . |
| 9004941 | 5/1990 | WIPO . |

OTHER PUBLICATIONS

Nicolai, "Über Sichtbarmachung, Verlauf und chemische Kinetik der Oxyhämoglobinreduktion im Lebenden Gewebe, besonders in der menschlichen Haut", 1932, pp. 372–384.

Matthes, "Untersuchungen über die Sauerstoffsättigung des menschlichen Arterienblutes", 1935, pp. 698–711.

Squire, "An instrument for measuring the quantity of blood and its degree of oxygenation in the web of the hand", 1940, pp. 331–337.

Millikan, "The Oximeter, an Instrument for Measuring Continuously the Oxygen Saturation of ARterial Blood in Man", Physical Instruments for the Biologist, Oct. 1942, vol. 13, pp. 434–444.

Wood and Geraci, "Photoelectric determination of arterial oxygen saturation in man", 1949, pp. 387–401.

Aoyagi et al., "Improvement of an Earpiece Oximeter", Abstracts of the 13th annual meeting of the Japanese Society for Medical Electronics and Biomedical Engineering, Osaka, JSMEBE, 1974, pp. 90–91.

Nakajima et al., "New Pulsed-type Earpiece Oximeter", 1975, pp. 709–713.

Yoshiya et al., "Spectrophotometric monitoring of arterial oxygen saturation in the fingertip", Medical & Biological Engineering & Computing, Jan. 1980, pp. 27–32.

Shimada et al., "Effects of multiple scattering and peripheral circulation on arterial oxygen saturation measured with a pulse-type oximeter", Medical & Biological Engineering & Computing, Sep. 1984, pp. 475–478.

Payne and Severinghaus, "Spectrophotometry and Oximetry", Pulse Oximetry, Chapter 1, Historical Development of Oxygenation Monitoring, 1985, pp. 1–18.

Primary Examiner—Angela D. Sykes
Attorney, Agent, or Firm—Spencer, Frank & Schneider

[57] ABSTRACT

An apparatus for measuring arterial elasticity includes a cuff member having a light source and light detector, a variable pressure generating device, a fluid pressure sensor, a digital signal processor and a difference detecting element. The fluid pressure in a fluid pressure chamber in the cuff member is varied by a variable fluid pressure generating device. The digital signal processor responds to the output of the fluid pressure sensor and the output of the difference detecting element and delivers a digitally processed signal corresponding to an arterial volume change based on a simulated arterial elasticity. The arterial elasticity and the frequency characteristic thereof are derived based on the operation of the digital signal processor.

11 Claims, 10 Drawing Sheets

Fig. 1

(PRIOR ART)

Fig. 2

(PRIOR ART)

MEASUREMENT OF ARTERIAL ELASTICITY AND THE FREQUENCY CHARACTERISTIC OF THE COMPLIANCE OF AN ARTERY

CROSS-REFERENCE TO RELATED APPLICATION

This application is a continuation-in-part of an earlier application, Ser. No. 07/695,008, filed May 3, 1991 now abandoned. The disclosure of this earlier application is incorporated herein by reference.

BACKGROUND OF THE INVENTION

1. Field of the Invention

The present invention relates to an apparatus and a method for measuring arterial elasticity. The apparatus according to the present invention can be used for noninvasively measuring the degree of sclerosis of an artery during diagnosis and treatment of the human body.

2. Description of the Related Arts

Recently attempts have been made to measure vascular viscoelasticity by using the relationship between the pressure and the volume of an artery. This measurement of vascular viscoelasticity, preferably the frequency characteristic of the viscoelasticity as well as the viscoelasticity itself, provides a measure of the degree of sclerosis of an artery.

There have been proposed, for example, a method of measuring arterial elasticity in human fingers using photoelectric plethysmography, and a volume compensation type method of measuring arterial elasticity in human fingers together with the frequency characteristic thereof, using photoelectric plethysmography.

In the method of measuring arterial elasticity using photoelectric plethysmography, it is assumed that Pas represents the systolic arterial pressure, Pam the mean arterial pressure, I the light intensity transmitted across the tissues, $\Delta I$ the changes in transmitted light intensity, and $I_t$ the light intensity transmitted across incompressible tissues other than the arterial systems. Under the above assumptions, the volume elastic modulus $E_v$ is derived according to the following equation.

$$E_v = 3/2 \ (P_{as} - P_{am}) / \{(\Delta I/I)\log(I/I_t)\}$$

In the volume compensation type method of measuring arterial elasticity, together with the frequency characteristic thereof, a sinusoidal change $\Delta P$ of the transmural pressure $P_t$ having a given frequency is applied to an artery of a finger of a human body, and the corresponding change $\Delta V$ of the volume of the artery is measured.

In fact, an artery is not a simple elastic tube but a tube having a striking viscoelastic property. The value of the change $\Delta V$ of the volume of the artery is changed, even under the same pulse pressure, due to a change of the frequency component of the waveform of the blood pressure caused by a change in the heart rate or blood pressure, and preferably the volume elastic modulus $E_v$ may be expressed is represented in association with the frequency characteristic. To facilitate an easy understanding of this, $E_v$ may be expressed as a transfer function to determine a volume change ratio $\Delta V/V$ caused by a transmural pressure change $\Delta P$.

The method of measuring arterial elasticity using photoelectric plethysmography is described, for example, in A. Kawarada et al.: "Noninvasive Automatic Measurement of Arterial Elasticity in Human Fingers and Rabbit Forelegs Using Photoelectric Plethysmography", Medical & Biological Engineering & Computing, Vol. 24, No. 6, P. 591 to 596, November 1986. The volume compensation type method of measuring arterial elasticity together with the frequency characteristic thereof is described, for example, in H. Shimazu et al.: "Noninvasive Measurement of Frequency Characteristics of Arterial Elastic Modulus in Human Fingers", Proceedings of 26th Conference of Japan Society of Medical Electronics & Biological Engineering, P. 213, Apr. 1 to 3, 1987.

In the above-mentioned first method for measuring arterial elasticity, however, problems have arisen in that the correct arterial elasticity cannot be measured because of the use of an estimated value for the pulse pressure value, and in that the frequency characteristic of the arterial elasticity cannot be obtained.

Also, in the above-mentioned second method, of the volume compensation type, for measuring arterial elasticity, a problem has arisen in that the volumetric pulse wave of two fingers, such as the index finger and the third finger, is different and accordingly, the motion of the artery can be eliminated in the index finger but cannot be eliminated in the third finger, even if the same pressure change is applied to these two fingers, and thus errors occur in the measurement of the arterial elasticity.

Further, in the above-mentioned second method, i.e., the volume compensation type, of measuring arterial elasticity, it is necessary to apply a sinusoidal pressure change and to scan the frequency of the pressure change, and accordingly, a relatively long time on the order of minutes is needed to determine the frequency characteristic of the arterial elasticity.

SUMMARY OF THE INVENTION

An object of the present invention is to provide an improved method of measuring arterial elasticity, in which the arterial elasticity together with the frequency characteristic thereof are measured in a very short time and with high precision.

Another object of the present invention is to provide an improved method of measuring arterial elasticity, by using a relatively simple apparatus and only one human finger with only one occluding cuff.

In accordance with the present invention, there is provided an apparatus for measuring arterial elasticity, including:

a cuff member having therein a light source and a light detector for accommodating an object to be measured and for transmitting a light through the object;

light source drive means connected to the light source for driving the light source;

a variable pressure generating means connected to a pressure chamber in the cuff member for supplying a varying fluid pressure in the form of random noise to the pressure chamber;

a fluid pressure sensor coupled to a fluid passage to said pressure chamber for detecting the varying fluid pressure in the form of random noise in the fluid passage;

a digital signal processor operating in response to a signal corresponding to the output of the pressure sensor and an output signal of a difference detecting element to deliver a digitally processed signal corresponding to an arterial volume change based on an arterial elasticity to be supplied to the difference detecting element; and a difference detecting element, in response to one input signal corresponding to the output of the light detector and the output signal of the digital signal processor as the other input signal to produce a signal representing the difference between the two input signals to be supplied to the digital signal processor;

the arterial elasticity and the frequency characteristic thereof being derived based on the operation of the digital signal processor.

In accordance with the present invention, there is also provided a method for measuring arterial elasticity including the steps of:

varying in the manner of random noise the fluid pressure in a cuff member applied to a finger as an object to be measured;

receiving a light emitted from a light source in the cuff member and transmigrated through the finger to which the fluid pressure in the cuff member is applied by a light detector, and measuring the transmitted light intensity; and carrying out adaptive signal processing by a digital signal processor based on the fluid pressure data representing the fluid pressure in the cuff member and the transmitted light data representing the intensity of the light transmitted through the finger;

whereby the arterial elasticity of the finger and the frequency characteristic thereof are determined eliminating the correlation between the fluid pressure in the cuff member and the arterial volume change due to the arterial internal blood pressure.

DESCRIPTION OF THE PREFERRED EMBODIMENTS

Figure 2:
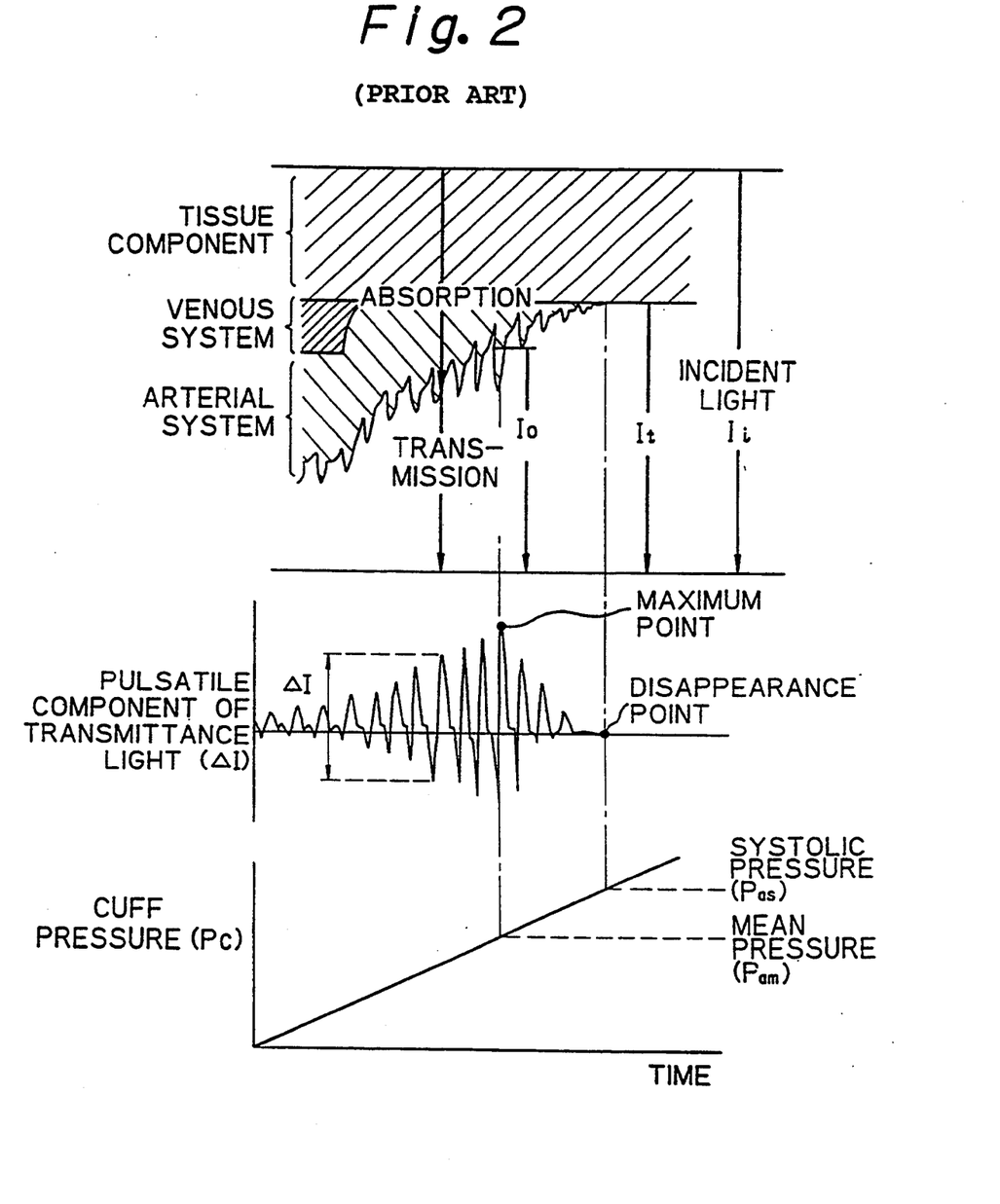
FIG. 2 shows characteristics of the operation of the arrangement of FIG. 1.
Figure 3:
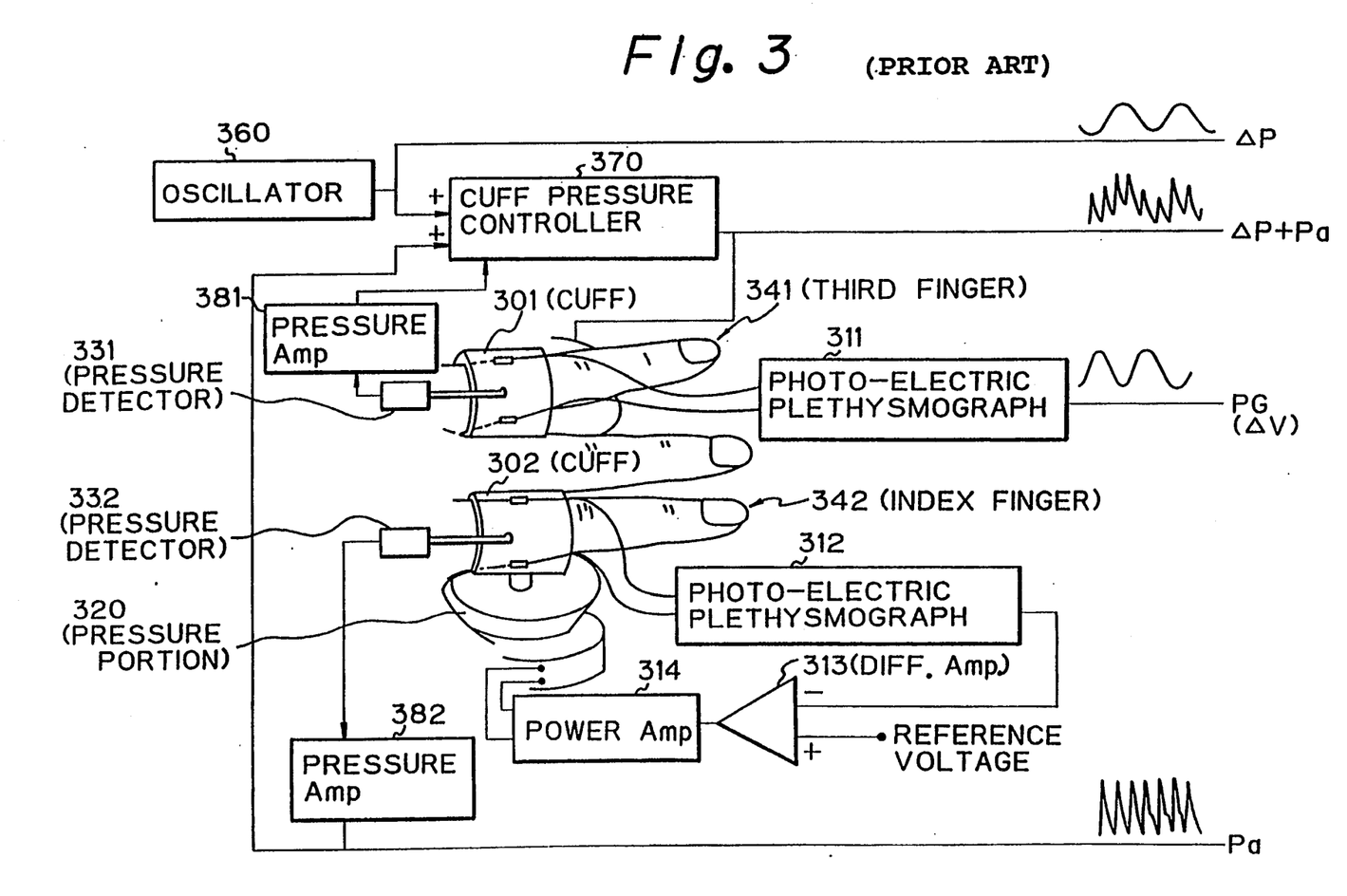
FIG. 3 illustrates an arrangement for another prior art method of measuring arterial elasticity.

Before describing the preferred embodiments, prior art methods of measuring arterial elasticity will be explained with reference to FIGS. 1; 2, and 3. A first prior art method of measuring arterial elasticity will be explained with reference to FIGS. 1 and 2. In the arrangement shown in FIG. 1, a plethysmograph is constituted by an occluding cuff 101, a light source 102, and a light detector 103 attached to the skin surface on the opposite sides of a human finger 104. The changes $\Delta I$ in the transmitted light intensity I, i.e., the pulsatile component of the transmittance light ($\Delta I$), following a gradual increase in the cuff pressure $P_c$ are shown in FIG. 2.

The intensity $I_i$ of the incident light, the mean transmitted light intensity $I_t$ across the tissue, and the light intensity $I_o$ corresponding to the maximum amplitude of $\Delta I$, are indicated. The indirect systolic arterial pressure Pas and the mean arterial pressure Pam are determined as the cuff pressures corresponding to the disappearance of, and the maximum peak of, the $\Delta I$ signal, respectively.

Figure 1:
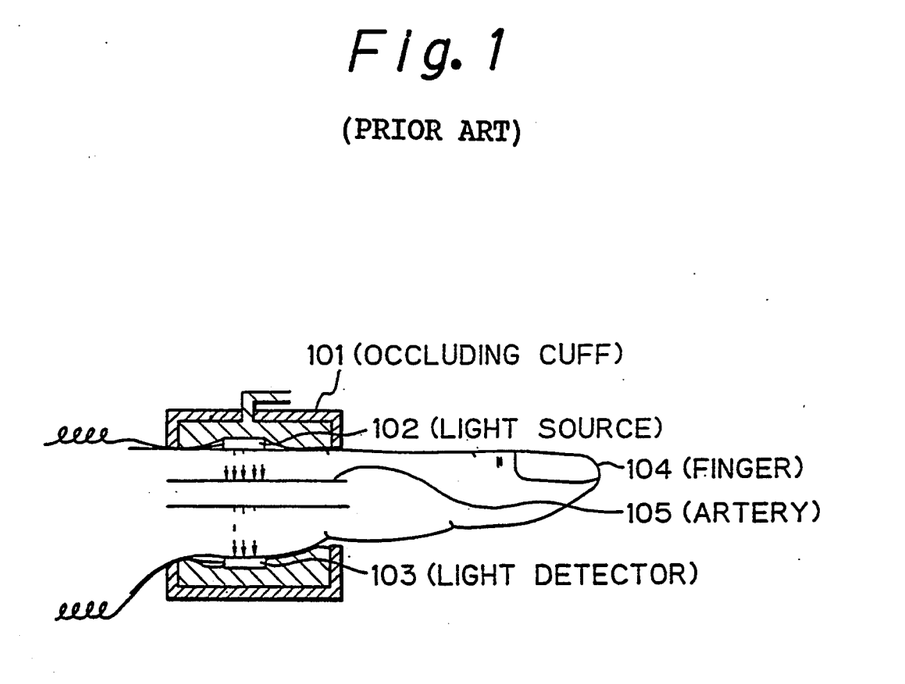
FIG. 1 illustrates an arrangement for a prior art method of measuring arterial elasticity.

In the operation of the arrangement of FIG. 1, the volume elastic modulus $E_v$ is determined in accordance with the following equation.

$$E_v = 3/2 \ (P_{as} - P_{am})/\{\Delta I/I)/\log(I/I_t)\}$$

A second prior art method of measuring arterial elasticity will be explained with reference to FIG. 3. A cuff 301 is coupled to the third finger 341 and another cuff 302 is coupled to the index FIG. 342, and the light sources and the light detectors in the cuffs 301 and 302 are connected to photoelectric plethysmographs 311 and 312. The cuff 301 is controlled by a cuff pressure controller 370, and the pressure in the cuff 301 is detected by a pressure detector 331, the output of which is amplified in a pressure amplifier 381 and output to the cuff pressure controller 370. The cuff 302 is pressurized by a pressure portion 320, such as a speaker. The pressure in the cuff 302 when the cuff is pressurized is detected by a pressure detector 332, the output of which is amplified in a pressure amplifier 382 and output to the cuff pressure controller 370.

The output of the photoelectric plethysmograph 312 is supplied to a differential amplifier 313, which produces the difference thereof from a reference voltage, and the output of the differential amplifier is supplied through a power amplifier 314 to the pressure portion 320. The cuff pressure controller 370 is supplied with the output of a frequency variable sinusoidal type oscillator 360. The cuff 302, the photoelectric plethysmograph 312, the differential amplifier 313, the power amplifier 314, the pressure detector 332, the pressure portion 320, and the pressure amplifier 382 constitute the portion used for the volume compensation method, and the remaining portion constitutes the portion used for the measurement.

The pressure in the cuff 302 is controlled such that the amount of light transmitted through the index finger 342 is made constant, i.e., the pressure Pa in the cuff 302 is made equal to the blood pressure, and the third finger 341 is subjected to the same pressure. In this case, the diameter of the artery of the third finger 341 is considered to be constant, and the arterial elasticity of the third finger is measured by applying an external pressure thereto.

A sinusoidal pressure $\Delta P$ having a predetermined frequency and the pressure Pa in the cuff 302 are superimposed, and the superimposed pressure is applied to the third finger 341. Under this condition, the arterial elasticity at the predetermined frequency is obtained by measuring the volume change $\Delta V$. The frequency characteristic of the arterial elasticity is obtained by scanning the frequency of the pressure change.

Figure 4:
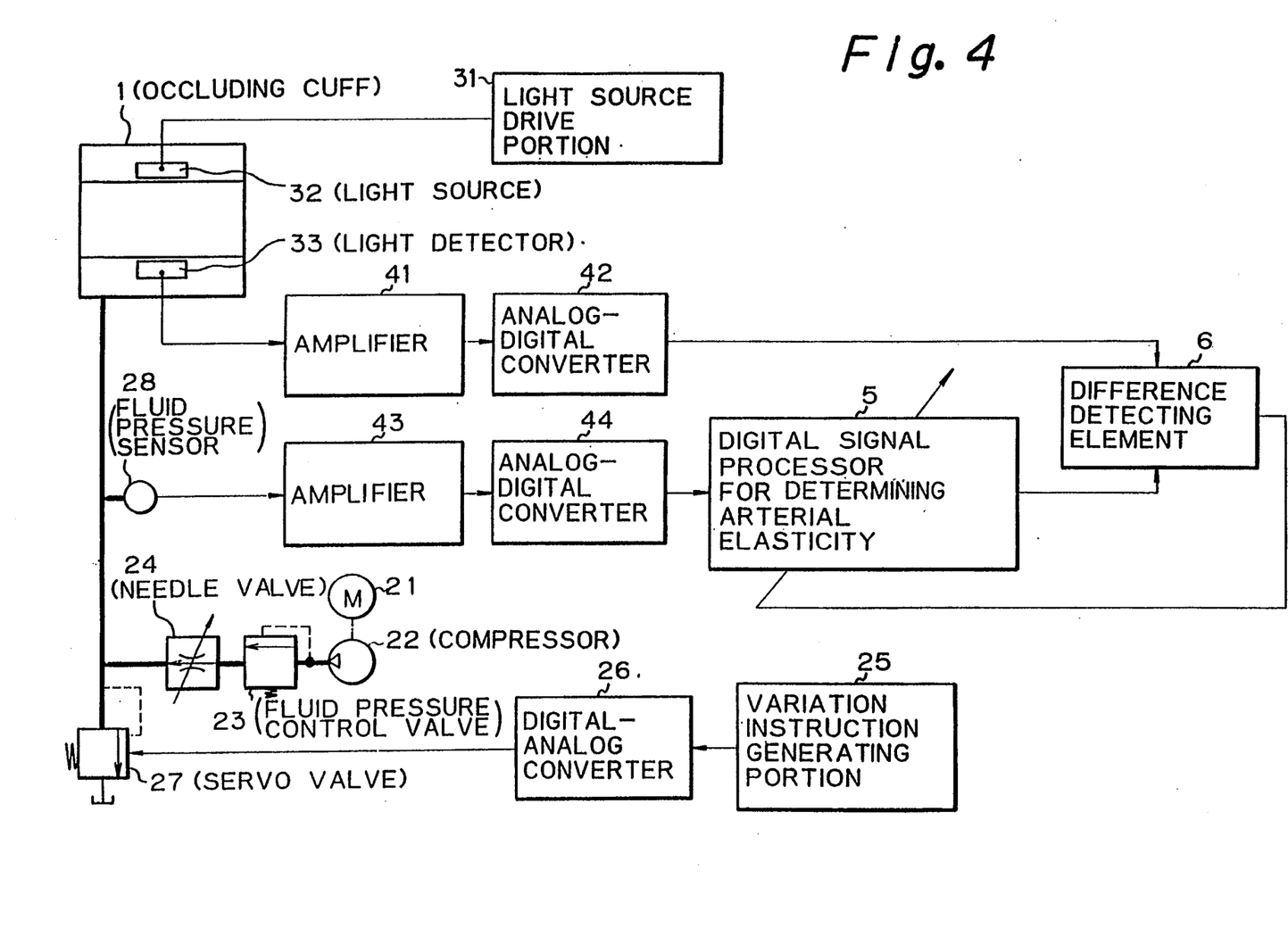
FIG. 4 illustrates a system for carrying out a method of measuring arterial elasticity according to an embodiment of the present invention.

A system for carrying out a method of measuring arterial elasticity according to an embodiment of the present invention is illustrated in FIG. 4. The system of FIG. 4 is provided with an occluding cuff 1, a motor 21, a compressor 22, a pressure control valve 23, a needle valve 24, a random signal generator 25 as a variation instruction generating portion 25, a digital-analog converter, a servo valve 27, and a pressure sensor 28. Also provided are a light source drive portion 31, a light source 32 such as a light emitting diode, and a light detector 33 such as a photo diode. Further, provided are amplifiers 41 and 43, analog-digital converters 42 and 44, a digital signal processor 5 for determining an arterial elasticity, and a difference detecting element 6.

The motor 21, the compressor 22, the pressure control valve 23, the needle valve 24, the random signal generator 25, the digital-analog converter 26, and the servo valve 27 constitute a varying cuff pressure generating unit. The cuff pressure in the form of random noise generated by this unit is supplied to the cuff 1, and the pressure in the cuff 1 is detected by the pressure sensor 28.

The output of the light detector 33 is amplified in the amplifier 41, the output of which is analog-digital converted in the analog-digital converter 42 and output to one input terminal of the difference detecting element 6. The output of the pressure sensor 28 is amplified in the amplifier 43, the output of which is analog-digital converted in the analog-digital converter 44 and output to one input terminal of the digital signal processor 5, for determining the arterial elasticity.

For the digital signal processor 5, a digital signal processor µPD77230 manufactured by NEC (Nippon Electric Corporation) may be used, for example, accompanied by an external random access memory for storing data such as adaptive filter coefficients, and for storing a fluid pressure data reading program, an adaptive signal processing program, and the like. This digital signal processor performs 32 bit floating point calculations at a speed of 150nsec per instruction in accordance with predetermined programs.

Figure 5:
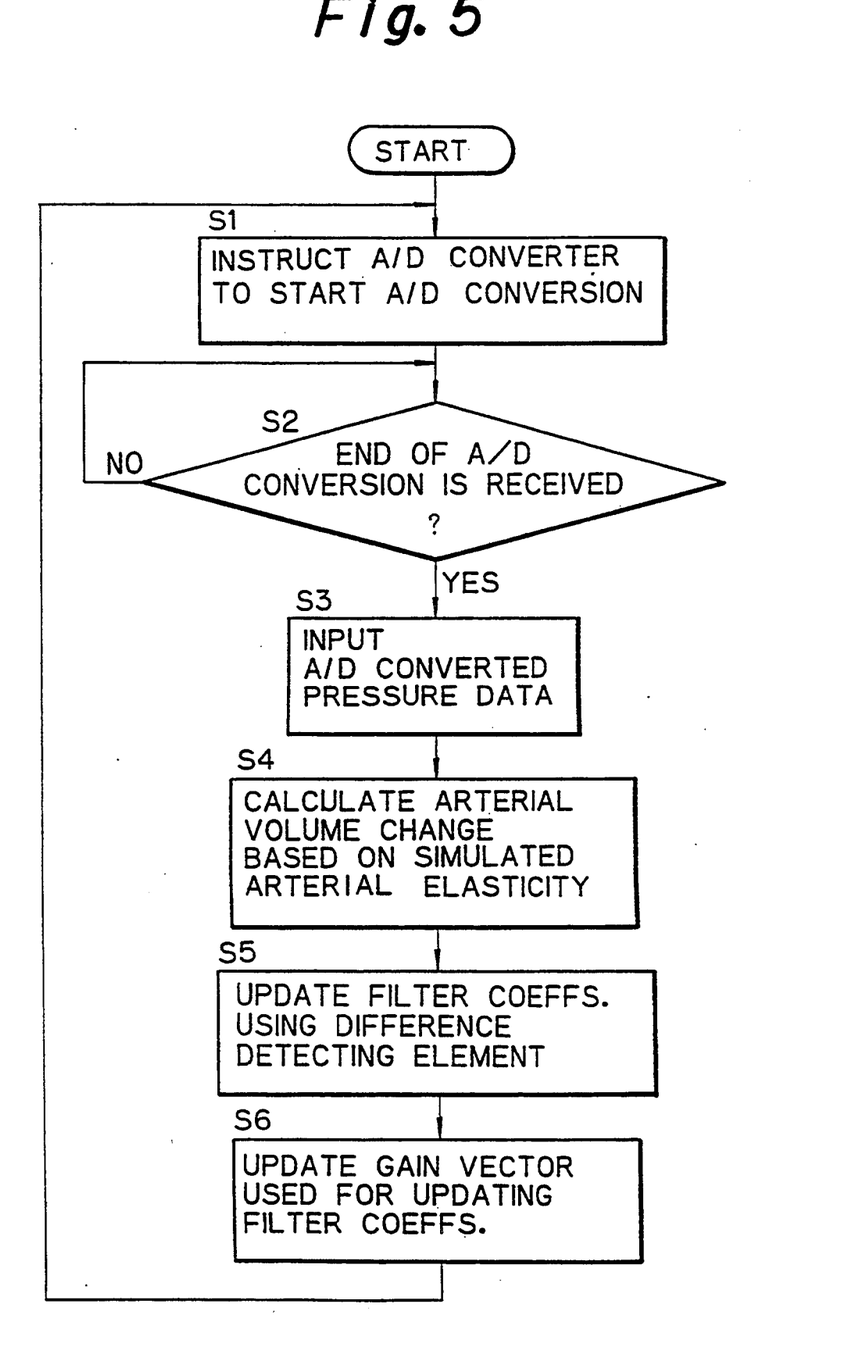
FIG. 5 shows a flow chart of the operation of the digital signal processor.

The operation of the digital signal processor 5 will be explained with reference to the flow chart of FIG. 5. In step S1, the analog-digital converter 44 is instructed to start an analog-digital conversion. In step S2, it is decided whether or not the signal of the end of the analog-digital conversion has been received. When the result of the decision is YES, the process proceeds to step S3 where the analog-digital converted fluid pressure data is input. In step S4, the arterial volume change is calculated based on the simulated arterial elasticity. In step S5, the filter coefficients are updated using the output of the difference detecting element 6. In step S6, the gain vector which is used for updating the filter coefficients is updated.

Figure 6:
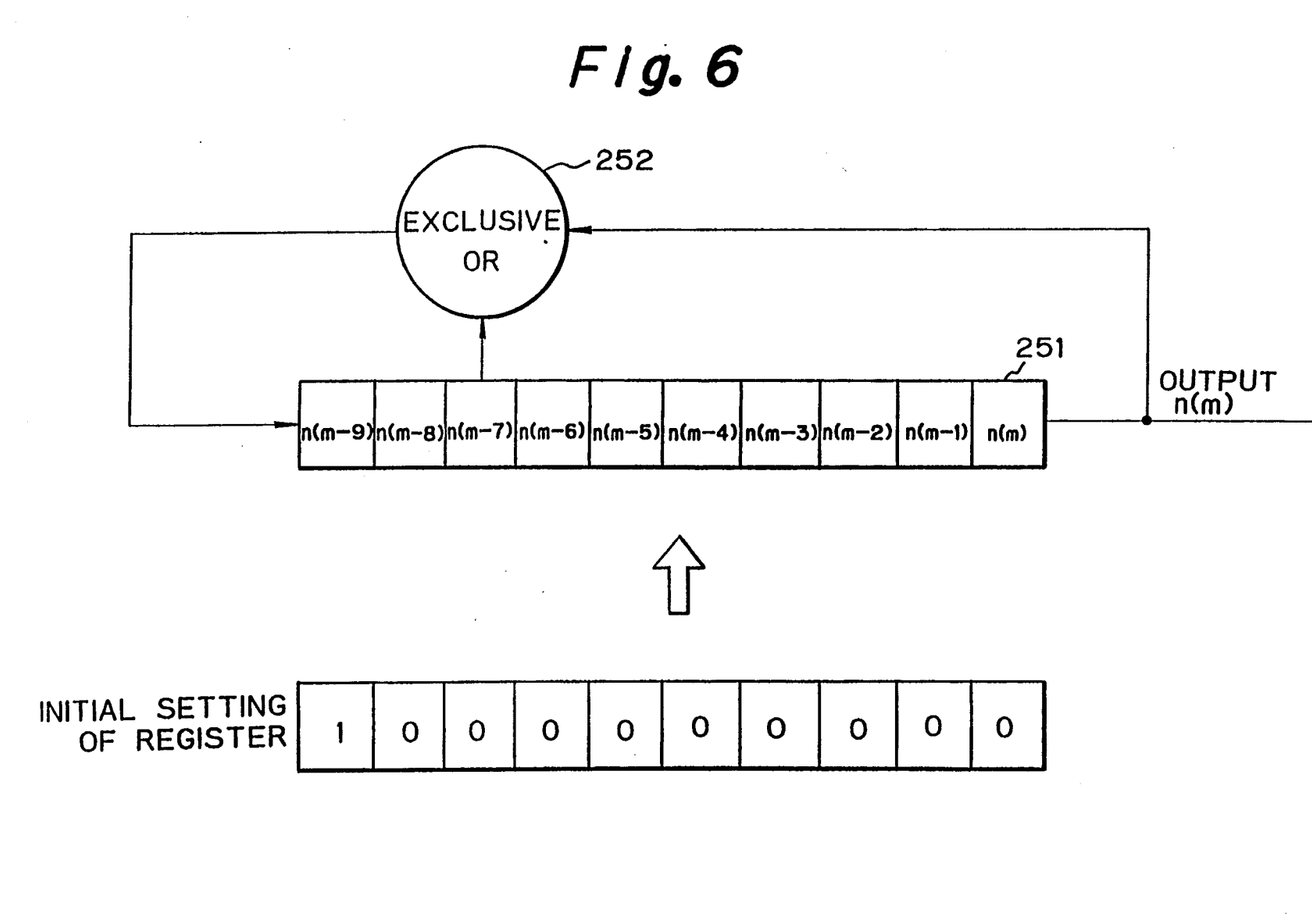
FIG. 6 shows the constitution of the random signal generator used in the vibration instruction generating portion.

The random signal generator used in the variation instruction generating portion 25 will be explained with reference to FIG. 6. The random signal generator shown in FIG. 6 is constituted by an M sequence register 251 having a length of 10 and an exclusive OR gate 252. The exclusive OR gate 252 receives the value of the 3rd register element and the value of the 10th element, i.e. the final element, and delivers the result of the logical exclusive OR operation to the 1st register element. The output n(m) of the register 251 gives a random fluid pressure output at instant m.

Figure 7:
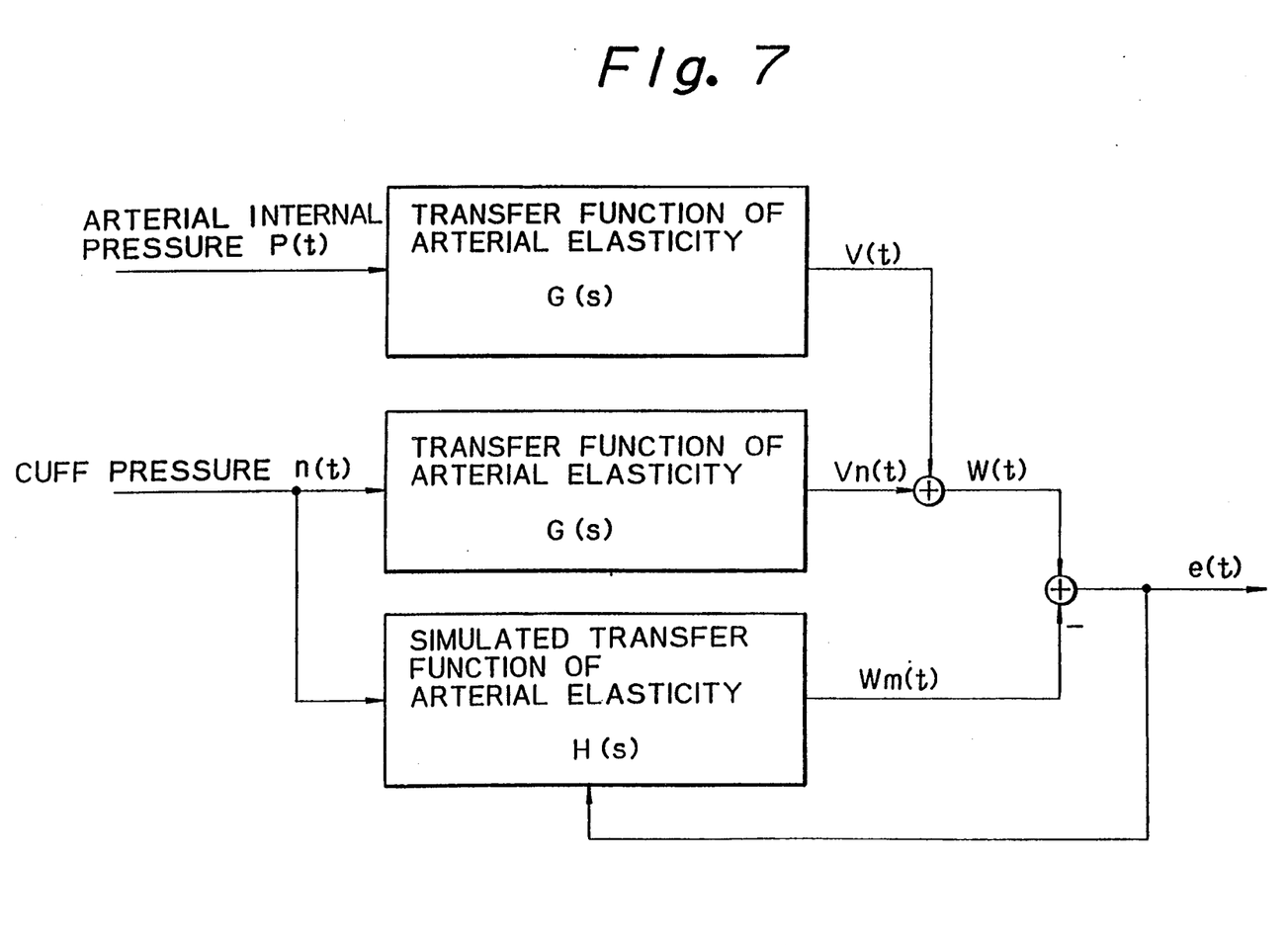
FIG. 7 illustrates the operation for calculating the arterial elasticity when measured by the system of FIG. 4.

The operation for calculating the elastic modulus of the artery when measured by the system of FIG. 4 is illustrated in FIG. 7.

A first transfer function G(S) of the arterial elasticity receives the arterial internal pressure P(t) and outputs the arterial volumetric change V(t). A second transfer function G(S) of the arterial elasticity, which is the same as the first transfer function, receives the cuff pressure n(t) and outputs the arterial volumetric change $V_n(t)$ due to cuff pressure. A simulated transfer function H(S) of the arterial elasticity receives the cuff pressure n(t) and outputs the signal $W_m(t)$.

The value V(t) from the first transfer function G(S) is added to the value $V_n(t)$ from the second transfer function G(S), to produce the value W(t); i.e., $W(t)=V(t)+V_n(t)$. The value $W_m(t)$ from the transfer function H(S) is subtracted from this value W(t) to produce an error value e(t); i.e., $e(t)=W(t)-W_m(t)$.

Each of the first and second transfer functions G(S) is expressed as a function of a variable S, which corresponds to the frequency, and as a compliance, which is the inverse of the elasticity.

If $W_m(t)$ is equal to $V_n(t)$, the simulated transfer function H(S) is regarded as having the same characteristic as the transfer function G(S), and therefore, it is possible to obtain the arterial elasticity and the frequency characteristic thereof from the simulated transfer function. This simulated transfer function can be realized by selecting the coefficients in the simulated transfer function such that the sum of the squares of the difference between W(t) and $W_m(t)$ is made a minimum value.

By randomly changing the cuff pressure, the influence of V(t) is eliminated, and accordingly the determination of G(S) is possible; where V(t) represents the change in the arterial volume and is considered a disturbance in the system identification.

The system of FIG. 4 is operated as follows. The occluding cuff 1 is fixed to a finger of which the arterial elasticity is to be determined. Then cuff pressure in the form of random noise is supplied from the varying cuff pressure generating unit to the cuff 1. The air output from the compressor 22 is supplied to the pressure control valve 23, where the pressure of the air is maintained at a predetermined constant pressure, the air output from the pressure control valve 23 is supplied to the needle valve 24, where the flow of the air is controlled, and the air output from the needle valve 24 is supplied to the cuff 1.

The amount of air exhausted from the servo valve 27 is controlled by controlling the displacement of an element of the servo valve 27 based on an instruction signal in accordance with a predetermined control mode from the random signal generator 25, through the digital-analog converter 26, and accordingly the cuff pressure is varied as random noise.

The light source 32 and the light detector 33 are placed opposite one another in the cuff 1, and the light emitted from the light source 32 driven by the output from the light source drive portion 31 is transmitted through the human finger and the transmitted light is received by the light detector 33. The light emitted from the light source 32 is preferably infrared light but can be visible light such as a red light.

The change of the amount of the transmitted light received by the light detector 33 corresponds to the change of the volume of blood in the artery, and the light detector 33 delivers an output signal in correspondence with the change of the volume of blood in the artery.

The output signal from the light detector 33 is amplified in the amplifier 41, the output of which is analog-digital converted in the analog-digital converter 42 and output to one input of the difference detecting element 6.

The cuff pressure in the form of random noise supplied to the cuff 1 is detected by the pressure sensor 28, and the pressure is transduced thereby into an electric signal. The signal from the pressure sensor 28 is amplified in the amplifier 43, the output of which is analog-digital converted in the analog-digital converter 44 and output to the one input of the digital signal processor 5 for determining the arterial elasticity. In the operations of the digital signal processor 5 for determining the arterial elasticity, and in the difference detecting portion 6, the coefficients of the transfer function are changed with time so that the output data based on the cuff pressure data becomes equal to the data of the amount of transmitted light, and when the coefficients are converged to predetermined constant values, the arterial elasticity and the frequency characteristic thereof are obtained based on the above-mentioned converged coefficients. Such an operation is called a system identification operation, and can be easily understood from the above explanation given with reference to FIG. 7.

Figure 8:
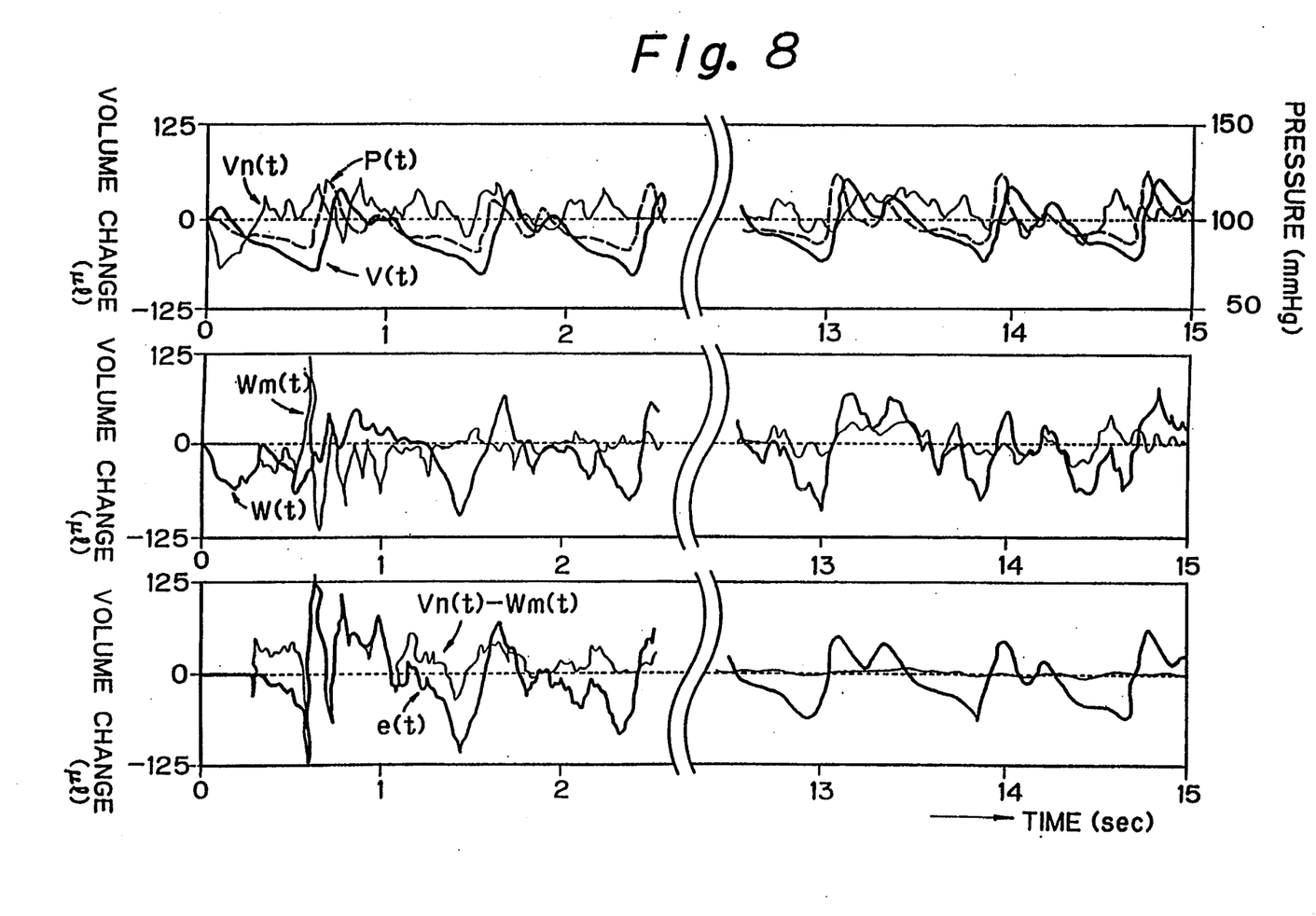
FIGS. 8 and 9 show examples of the simulation of the operation of the system for carrying out a method of measuring arterial elasticity according to an embodiment of the present invention.
Figure 9:
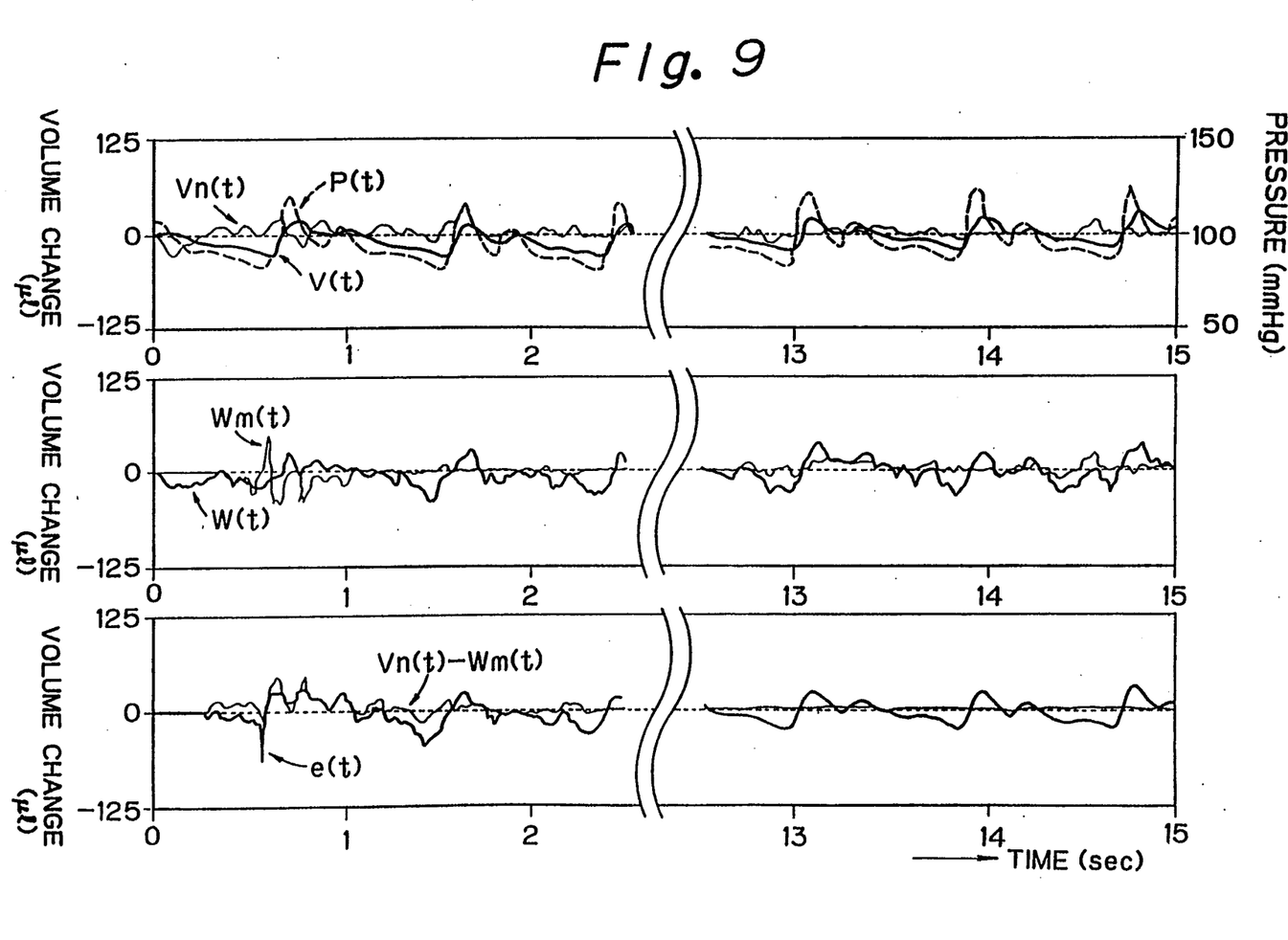

Examples of the simulation of the operation of the system carrying out a method according to an embodiment of the present invention are shown in FIGS. 8 and 9. The simulations of the operation of the digital signal processor 5 for determining arterial elasticity in the system of FIG. 4 are shown in FIGS. 8 and 9.

In the simulation of FIG. 8, where the internal/external arterial pressure difference is assumed to be zero, the abscissa represents time, and the ordinate represents arterial volume change in $\mu$l and the pressure in mmHg. The upper part represents the changes of $V_n(t)$, $P(t)$, and $V(t)$, the middle part represents the changes of $W_m(t)$ and $W(t)$, and the lower part represents the changes of "$V_n(t) - W_m(t)$".

Since arterial elasticity depends on the internal/external pressure difference $P_{tr}$ of an artery, the compliance of a linear first order delay system is assumed as $$5.2/(1+0.088S) \mu l/mmHg$$

when $P_{tr}$ 0 mmHg, and as $$1.8/(1+0.053S) \mu l/mmHg$$

when $P_{tr} = 60$ mmHg.

In the example shown in FIG. 8, the value of the blood pressure measured at the index finger of the left hand of a 27 year old male using the volume compression method is depicted. A simulation by an M sequence random signal with a 40 mmHg amplitude with a 20 Hz band limitation is used as the simulation. Further, a sampling frequency of 100 Hz, a 30 tap finite impulse response (FIR) type digital signal processor, and an algorithm of the recursive least square (RLS) method are used.

The digital signal processor is operated such that $W_m(t)$ becomes equal to $V_n(t)$, and the difference "$V_n(t) - W_m(t)$" is reduced as time passes and becomes nearly zero in about 15 seconds, as seen in the lower part of FIG. 8. In the lower part of FIG. 8, the waveform of e(t) reproduces the waveform of $V(t)$, which implies that the digital signal processor is normally operated.

In the simulation of FIG. 9, where the internal/external arterial pressure difference is assumed to be 60 mmHg, $V(t)$ and $V_n(t)$ are smaller than in the case of FIG. 8, since the compliance is smaller than in the case of FIG. 8. In the case of FIG. 9; the difference "$V_n(t) - W_m(t)$" is reduced as time passes and becomes nearly zero in about 15 seconds, similar to the case of FIG. 8. It will be observed in FIGS. 8 and 9 that the measurement of the arterial elasticity and the frequency characteristic thereof can be carried out in a very short time of about 15 seconds.

Figure 10:
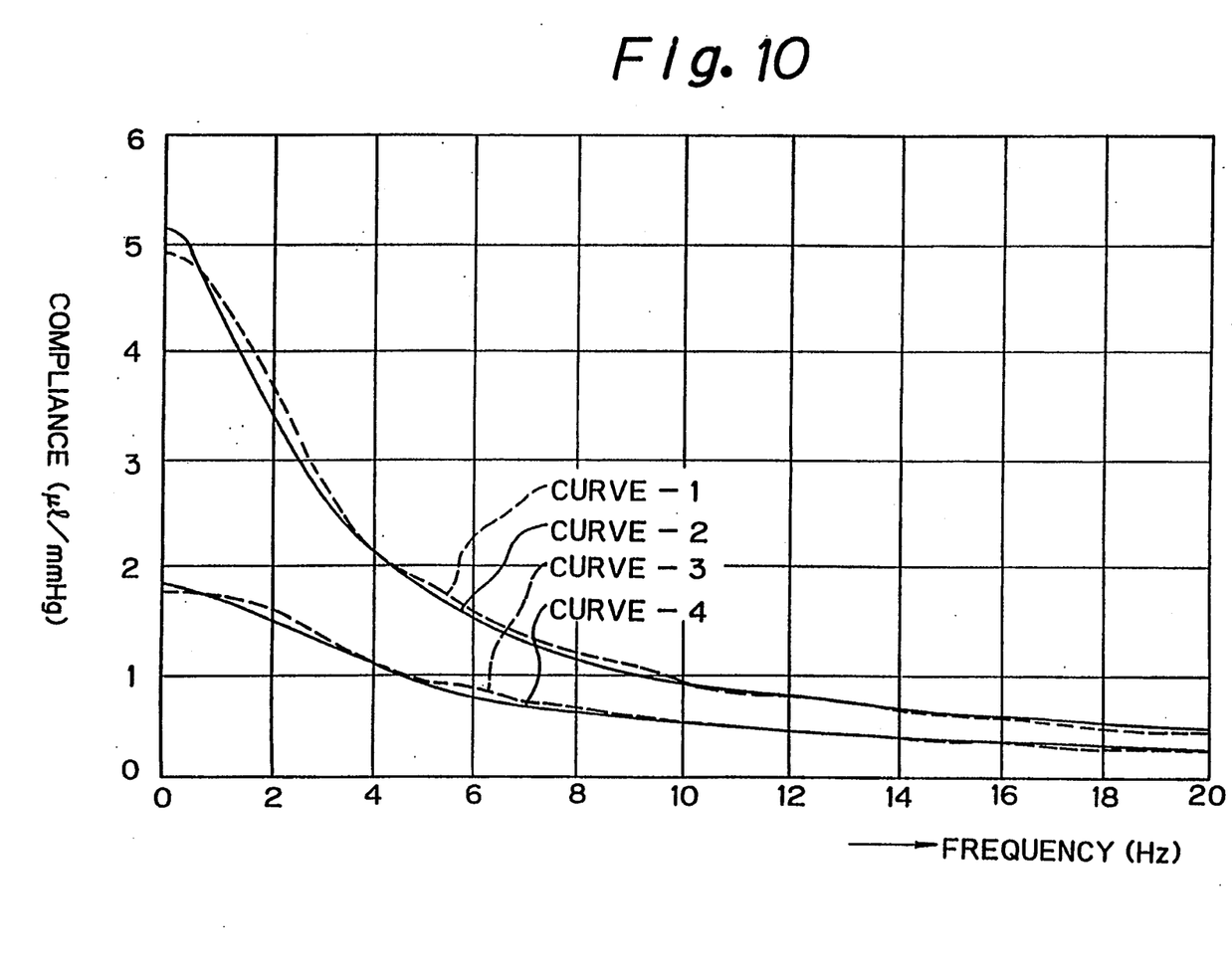
FIG. 10 shows an example of the frequency characteristic of arterial elasticity.

An example of the frequency characteristic of the arterial elasticity is shown in FIG. 10. In FIG. 10, the abscissa represents the frequency in Hz, and the ordinate represents the compliance in $\mu$l/mmHg. In FIG. 10, CURVE-1, as a broken line, represents the arterial elasticity obtained by the simulation with an internal/external arterial pressure difference of zero, CURVE-2, as a solid line, represents actual data of the arterial elasticity with an internal/external arterial pressure difference of zero, CURVE-3, as a broken line, represents the arterial elasticity obtained by the simulation with an internal/external arterial pressure difference of 60 mmHg, and CURVE-4, as a solid line, represents actual data of the arterial elasticity with an internal/external arterial pressure difference of 60 mmHg. It will be observed in FIG. 10 that the arterial elasticity obtained by the simulation, shown as a broken line, can satisfactorily reproduce the actual data of the arterial elasticity.

In summary, it will be apparent that the dynamic compliance of an artery is represented by a linear first order delay system in the foregoing examples. In general the term "compliance" refers to the relationship between the volume and the pressure of a hollow elastic body. The compliance of an artery varies with frequency and can be expressed as dV/dP, where dV is the change in the volume of the artery and dP is the change in the pressure exerted on the artery. Here, the arterial compliance is expressed by the transfer function of a first order delay system as follows:

$$dV/dP(s) = G(s) = K/(1+Ts) \mu l/mmHg$$

In this expression it is assumed that $K = 5.2$ and $T = 0.088$ when $P_{tr} = 0$ mmHg and that $K = 1.8$ and $T = 0.053$ when $P_{tr} = 60$ mmHg. H(s) is the transfer function of a linear first order delay system constituted by an adaptive filter in the digital signal processor 5. As was indicated above, the compliance of the artery and the frequency characteristic thereof are determined from the coefficients of the adaptive filter when G(s) coincides with H(s).

What we claim is:

1. An apparatus for measuring arterial elasticity and the frequency characteristic of the compliance of an artery to determine the degree of sclerosis of the artery, comprising:

a cuff member having therein a light source and a light detector for accommodating an object to be measured and for transmitting a light through the object;

light source drive means connected to said light source for driving said light source;

a variable fluid pressure generating means connected to a fluid pressure chamber in said cuff member for supplying a varying fluid pressure in the form of random noise to said fluid pressure chamber;

a fluid passage connected to said fluid pressure chamber;

a fluid pressure sensor means, coupled to said fluid passage, for detecting the varying fluid pressure in the form of random noise in said fluid passage, the fluid pressure sensor means providing an output indicative of the detected pressure;

a digital signal processor means, responsive to a signal corresponding to the output of said fluid pressure sensor means and responsive to a further signal, for delivering a digitally processed signal corresponding to an arterial volume change based on a simulated arterial elasticity; and a difference detecting means, responsive to one input signal corresponding to an output of said light detector and another input signal corresponding to the digitally processed output signal of said digital signal processor means, for producing a signal which represents the difference between the two input signals and which is supplied to said digital signal processor means as the further signal;

arterial elasticity and the frequency characteristic of the compliance of the artery being derived based on the operation of said digital signal processor means to determine the degree of sclerosis of the artery.

2. An apparatus according to claim 1, wherein said digital signal processor means and said difference detecting means operate as an adaptive filter.

3. An apparatus according to claim 1, wherein said digital signal processor means and said difference detecting means process a system identification.

4. An apparatus according to claim 1, wherein said digital signal processor means and said difference detecting means calculate an error value, using transfer functions of arterial elasticity, a simulated transfer function of arterial elasticity, and summing elements.

5. A method for measuring arterial elasticity and the frequency characteristic of the compliance of an artery in a finger to determine the degree of sclerosis of the artery, comprising the steps of;

varying fluid pressure in a cuff member applied to the finger as an object to be measured, including varying the fluid pressure in the form of random noise;

receiving, by a light detector, a light emitted from a light source in the cuff member and transmitted through the finger to which the fluid pressure in the cuff member is applied, and measuring the transmitted light intensity; and carrying out an adaptive signal processing by a digital signal processor based on fluid pressure data representing the fluid pressure in the cuff member and the transmitted light data representing the intensity of the light transmitted through the finger;

wherein said method measures arterial elasticity of the finger and the frequency characteristic of the compliance of the artery in the finger to determine the degree of sclerosis of the artery eliminating a correlation between the fluid pressure in the cuff member and an arterial volume change due to an arterial internal blood pressure.

6. An apparatus for measuring arterial elasticity, comprising:

a cuff for receiving a body member, the cuff having a light source, a light detector which generates a light detector signal, and a fluid pressure chamber;

variable pressure generating means for supplying fluid pressure which varies in a non-periodic manner to the fluid pressure chamber;

means for generating a pressure signal which is indicative of the fluid pressure in the fluid pressure chamber; and means for determining the arterial elasticity in response to the light detector signal and the fluid pressure signal, the means for determining including a digital signal processor which receives first and second input signals and which generates an output signal, the first input signal corresponding to the pressure signal, and means for generating a difference signal which represents the difference between the output signal of the digital signal processor and a signal which corresponds to the light detector signal, the difference signal serving as the second input signal to the digital signal processor.

7. The apparatus of claim 6, wherein the variable pressure generating means comprises a conduit connected to the fluid pressure chamber, means for supplying a flow of air to the conduit, a servo valve connected to the conduit to selectively release air from the conduit, means for generating a non-repeating sequence of numbers, and means for controlling the servo valve in response to the non-repeating sequence of numbers.

8. The apparatus of claim 7, wherein the means for generating a non-repeating sequence of numbers comprises a register and an exclusive-OR gate connected to the register.

9. The apparatus of claim 6, wherein the digital signal processor and the means for generating a difference signal comprise an adaptive filter.

10. The apparatus of claim 6, wherein the digital signal processor and the means for generating a difference signal process a system identification.

11. The apparatus of claim 6, wherein the digital signal processor comprises a digital signal processor IC.

* * * * *